(12) United States Patent
Chernyak

(10) Patent No.: US 7,458,683 B2
(45) Date of Patent: Dec. 2, 2008

(54) METHODS AND DEVICES FOR REGISTERING OPTICAL MEASUREMENT DATASETS OF AN OPTICAL SYSTEM

(75) Inventor: Dimitri Chernyak, Sunnyvale, CA (US)

(73) Assignee: AMO Manufacturing USA, LLC, Santa Clara, CA (US)

(*) Notice: Subject to any disclaimer, the term of this patent is extended or adjusted under 35 U.S.C. 154(b) by 104 days.

(21) Appl. No.: 10/463,674

(22) Filed: Jun. 16, 2003

(65) Prior Publication Data
US 2004/0263785 A1 Dec. 30, 2004

(51) Int. Cl.
*A61B 3/10* (2006.01)

(52) U.S. Cl. .................................... 351/205

(58) Field of Classification Search ............... 351/200, 351/205, 211, 212, 221, 246, 206; 382/128, 382/293–298, 218, 219, 100, 115, 117; 600/398, 600/399; 604/289; 606/4–6; 607/53, 54; 128/922; 345/467–472.3
See application file for complete search history.

(56) References Cited

U.S. PATENT DOCUMENTS

| | | | |
|---|---|---|---|
| 4,540,254 A | 9/1985 | Humphrey | |
| 4,641,349 A | 2/1987 | Flom et al. | |
| 4,665,913 A | 5/1987 | L'Esperance, Jr. | |
| 4,761,071 A | 8/1988 | Baron | |
| 4,848,340 A | 7/1989 | Bille et al. | |
| 4,995,716 A | 2/1991 | Warnicki et al. | |
| 5,036,347 A | 7/1991 | Tsunekawa et al. | |
| 5,062,702 A * | 11/1991 | Bille | 351/212 |
| 5,070,883 A | 12/1991 | Kasahara | |
| 5,098,426 A | 3/1992 | Sklar et al. | |
| 5,159,361 A | 10/1992 | Cambier et al. | |
| 5,214,455 A | 5/1993 | Penney et al. | |
| 5,291,560 A * | 3/1994 | Daugman | 351/206 |
| 5,293,871 A | 3/1994 | Reinstein et al. | |
| 5,406,342 A | 4/1995 | Jongsma | |

(Continued)

FOREIGN PATENT DOCUMENTS

EP 0456166 A1 11/1991

(Continued)

OTHER PUBLICATIONS

Groen et al., "Video-Oculography" Chapter 1.PhD Thesis, The Dutch Experiment Support Center [online], 1997 [retrieved on Jul. 20, 2005]. Retrieved from the Internet: <URL: http://www.desc.med.vu.nl/Publications/Thesis/Groen/Groen_Chapter1.htm>.

(Continued)

*Primary Examiner*—Hung X. Dang
*Assistant Examiner*—Tuyen Q Tra
(74) *Attorney, Agent, or Firm*—Townsend and Townsend and Crew LLP

(57) ABSTRACT

The present invention provides methods, systems and software for registering a first dataset of an object with a second dataset of an object. In one embodiment, the present invention measures refractive errors of an optical system. The method comprises obtaining a first and second optical measurement of the optical system. The first and second optical measurements are registered with each other and may improve the diagnosis and/or treatment of the refractive errors of the optical system. In one embodiment the first optical measurement is a topographical map and the second optical measurement is a wavefront measurement.

49 Claims, 11 Drawing Sheets

U.S. PATENT DOCUMENTS

| | | | |
|---|---|---|---|
| 5,491,524 A | 2/1996 | Hellmuth et al. | |
| 5,512,965 A | 4/1996 | Snook | |
| 5,512,966 A | 4/1996 | Snook | |
| 5,549,597 A | 8/1996 | Shimmick et al. | |
| 5,550,937 A * | 8/1996 | Bell et al. | 382/293 |
| 5,572,596 A | 11/1996 | Wildes et al. | |
| 5,581,637 A * | 12/1996 | Cass et al. | 382/294 |
| 5,620,436 A | 4/1997 | Lang et al. | |
| 5,646,791 A | 7/1997 | Glockler | |
| 5,649,032 A * | 7/1997 | Burt et al. | 382/294 |
| 5,683,379 A | 11/1997 | Hohla | |
| 5,713,892 A | 2/1998 | Shimmick | |
| 5,740,803 A | 4/1998 | Gray et al. | |
| 5,777,719 A | 7/1998 | Williams et al. | |
| 5,843,070 A | 12/1998 | Cambier et al. | |
| 5,850,486 A * | 12/1998 | Maas et al. | 382/294 |
| 5,865,832 A | 2/1999 | Knopp et al. | |
| 5,891,132 A | 4/1999 | Hohla | |
| 5,923,399 A | 7/1999 | Van de Velde | |
| 5,951,475 A * | 9/1999 | Gueziec et al. | 382/294 |
| 5,963,300 A * | 10/1999 | Horwitz | 351/209 |
| 5,974,165 A * | 10/1999 | Giger et al. | 382/294 |
| 5,980,513 A | 11/1999 | Frey et al. | |
| 6,004,313 A | 12/1999 | Shimmick et al. | |
| 6,079,828 A | 6/2000 | Fujieda | |
| 6,095,651 A | 8/2000 | Williams et al. | |
| 6,104,828 A * | 8/2000 | Shioiri | 382/128 |
| 6,116,738 A | 9/2000 | Rorabaugh | |
| 6,129,722 A | 10/2000 | Ruiz | |
| 6,203,539 B1 | 3/2001 | Shimmick et al. | |
| 6,234,631 B1 * | 5/2001 | Sarver et al. | 351/212 |
| 6,245,059 B1 | 6/2001 | Clapham | |
| 6,266,453 B1 * | 7/2001 | Hibbard et al. | 382/294 |
| 6,271,915 B1 | 8/2001 | Frey et al. | |
| 6,305,802 B1 * | 10/2001 | Roffman et al. | 351/212 |
| 6,314,197 B1 * | 11/2001 | Jain et al. | 382/294 |
| 6,347,549 B1 | 2/2002 | Ryan et al. | |
| 6,351,573 B1 * | 2/2002 | Schneider | 382/294 |
| 6,393,163 B1 * | 5/2002 | Burt et al. | 382/294 |
| 6,394,999 B1 * | 5/2002 | Williams et al. | 606/5 |
| 6,396,069 B1 | 5/2002 | MacPherson et al. | |
| 6,413,251 B1 * | 7/2002 | Williams | 606/5 |
| 6,419,671 B1 | 7/2002 | Lemberg | |
| 6,496,594 B1 * | 12/2002 | Prokoski | 382/118 |
| 6,500,171 B1 * | 12/2002 | Williams et al. | 606/5 |
| 6,508,812 B1 * | 1/2003 | Williams et al. | 606/5 |
| 6,634,750 B2 * | 10/2003 | Neal et al. | 351/211 |
| 6,634,752 B2 * | 10/2003 | Curatu | 351/212 |
| 6,673,062 B2 | 1/2004 | Yee et al. | |
| 6,702,806 B2 | 3/2004 | Gray et al. | |
| 6,728,424 B1 * | 4/2004 | Zhu et al. | 382/294 |
| 6,793,654 B2 | 9/2004 | Lemberg | |
| 6,929,638 B2 | 8/2005 | Gray et al. | |
| 7,146,983 B1 | 12/2006 | Hohla et al. | |
| RE39,882 E | 10/2007 | Mihashi et al. | |
| 7,309,126 B2 | 12/2007 | Mihashi et al. | |
| 2003/0223037 A1 | 12/2003 | Chernyak | |
| 2004/0019346 A1 | 1/2004 | Chernyak | |
| 2004/0070730 A1* | 4/2004 | Mihashi et al. | 351/221 |
| 2004/0116910 A1* | 6/2004 | Markman | 606/5 |
| 2004/0169817 A1* | 9/2004 | Grotehusmann et al. | 351/204 |
| 2005/0007551 A1* | 1/2005 | Wakil et al. | 351/205 |
| 2005/0107775 A1* | 5/2005 | Huang et al. | 606/5 |

FOREIGN PATENT DOCUMENTS

| | | |
|---|---|---|
| EP | 0765648 A2 | 4/1997 |
| EP | 0770370 A2 | 5/1997 |
| EP | 1221890 A1 | 4/2001 |
| EP | 1153570 A1 | 11/2001 |
| EP | 1210003 A2 | 11/2001 |
| EP | 1280484 A0 | 2/2003 |
| EP | 1514509 A2 | 3/2005 |
| WO | 92/01417 A1 | 2/1992 |
| WO | 0001417 A1 | 2/1992 |
| WO | 94/18883 A1 | 9/1994 |
| WO | 95/27453 A1 | 10/1995 |
| WO | 95/11655 A1 | 4/1996 |
| WO | 99/27334 A1 | 6/1999 |
| WO | 00/27273 A1 | 5/2000 |
| WO | 01/11418 A1 | 2/2001 |
| WO | WO 01/11418 A1 | 2/2001 |
| WO | 01/66029 A1 | 9/2001 |
| WO | 01/78584 A2 | 10/2001 |
| WO | 01/85045 A1 | 11/2001 |
| WO | 01/85075 A1 | 11/2001 |
| WO | 02/087442 A1 | 11/2002 |
| WO | WO9316631 | 5/2007 |

OTHER PUBLICATIONS

Bos and de Graaf, "Ocular Torsion Quantification with Video Images," IEEE Transactions on Biomedical Engg., vol. 41, No. 4, Apr. 1994, pp. 351-357.

Markham and Diamond, "Eye Torsion in Space and during Static Tilt Pre- and Post-Spaceflight," Proceedings of the 6th European Symposium on Life Sciences Research in Space, Trondheim, Norway 1996 ESA SP-390 (Oct. 1996), p. 89.

Sensomotoric Instruments GmbH, "Opposition Against European Patent No.: 1 221 922 B1", filed Jun. 27, 2007, 41 total pages.

Koch, Refractive Surgical Problem, edited by Thomas Kohnen, MD, J. Cataract Refract Surg, vol. 24, No. 7, Jul. 1998, pp. 876-881, <<http://www.ascrs.org/publications.jcrs.jcrsindex.html>>.

Suzuki A., et al., "Using a Reference Point and Videokeratography for Inoperative Identification of Astigmatism Axis", J. Cataract Refract. Surg., vol. 23, No. 10, Dec. 1997, pp. 1491-1495.

Suzuki et al., Refractive Surgical Problem, edited by Thomas Kohnen, MD, J. Cataract Refract Surg, vol. 24, No. 7, Jul. 1998, pp. 876-881, <<http://ascrs.org/publications/jcrs/jcrsindex.html>>.

Liang et al., "Objective Measurement of Wave Abberrations with the Use of a Hartmann-Shack Wave-front Sensor", J. Opt. Soc. of America., vol. 11, No. 7, Jul. 1994, pp. 1-9.

Liang & Williams, "Aberrations and Retinal Image Quality of the Normal Human Eye," J. of the Opt. Soc. of Amer., vol. 4, No. 11, Nov. 1997, pp. 2873-2883.

Kremer, Frederick B., "How to Keep Lasik on Axis," Review of Ophthamology, Mar. 1999, <<http://www.revophth.com/1999/march_articles/rpc9q&a.html>>, 1 page only.

Yamanobe et al., "Eye Movement Analysis System Using Computerized Image Recognition," Arch Otolaryngol Head Neck Surg., vol. 116, No. 3, Mar. 1990, pp. 338-341.

Uozato et al., "Centering Surgical Procedures," American J. Ophthal., vol. 103, Mar. 1987, pp. 264-275.

Groen et al., "Determination of Ocular Torsion by Means of Automation Pattern Recognition," IEEE Trans Biomed. Eng., May 1996, vol. 43, No. 5, pp. 471-479.

Leventon, Michael Emmanuel, "A Registration, Tracking and Visualization System for Image Guided Surgery," Master-Thesis, MIT 1997, 123 pages total.

Chiron Technolas GmbH, Keracor Excimer Laser System, User Manual Version 1.0, Aug. 1996, 61 pages total.

Visx Incorporated, "Opposition Against European Patent No.: 1 221 922 B1", filed Jun. 26, 2007, 28 pages total.

Autonomous Technologies Corporation, Tracker-Assisted Photorefractive Keratectomy System (T-PRK®) Operation Manual, SEp. 2, 1997, 8 pages total. p. 27, 43-48.

Sensomotoric Instruments GmbH, "VOG for Windows User Manual," version 3.08, Nov. 1996, 280 pages total, pp. 1-279.

* cited by examiner

METHODS AND DEVICES FOR REGISTERING OPTICAL MEASUREMENT DATASETS OF AN OPTICAL SYSTEM

CROSS-REFERENCES TO RELATED APPLICATIONS

The present application is related to U.S. patent application Ser. No. 10/300,714, filed Nov. 19, 2002, which claimed the benefit of U.S. Provisional Patent Application Ser. No. 60/384,653, filed May 30, 2002, the complete disclosures of which are incorporated herein by reference.

The present application is also related to U.S. patent application Ser. No. 10/365,121, filed Feb. 11, 2003, which claimed the benefit of Provisional Patent Application No. 60/356,658, filed Feb. 11, 2002 and U.S. Patent Application Ser. No. 60/389,090, filed Jun. 13, 2002, the complete disclosures of which are incorporated herein by reference.

BACKGROUND OF THE INVENTION

The present application relates generally to registering multiple datasets with each other. More specifically, the present invention relates to registering a wavefront measurement and a corneal topography map of an eye.

Known laser eye procedures generally employ an ultraviolet or infrared laser to remove a microscopic layer of stromal tissue from the cornea of the eye to alter the refractive characteristics of the eye. The laser removes a selected shape of the corneal tissue, often to correct refractive errors of the eye. Ultraviolet laser ablation results in photo-decomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of a pattern of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, thermal shaping, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to measure the refractive characteristics of a particular patient's eye.

One promising wavefront measurement system is the VISX WaveScan® System, which uses a Hartmann-Shack wavefront sensor assembly that may quantify higher-order aberrations throughout the entire optical system, including first and second-order sphero-cylindrical errors and third through sixth-order aberrations caused by coma and spherical aberrations. The wavefront measurement of the eye creates a high order aberration map that permits assessment of aberrations throughout the optical pathway of the eye, e.g., both internal aberrations and aberrations on the corneal surface. Thereafter, the wavefront aberration information may be saved and thereafter input into a computer system to compute a custom ablation pattern to correct the aberrations in the patient's eye.

By customizing an ablation pattern based on wavefront measurements, it may be possible to correct minor refractive errors so as to reliably and repeatably provide visual accuities greater than 20/20. Alternatively, it may be desirable to correct aberrations of the eye that reduce visual acuity to less than 20/20.

While wavefront measurement systems have been highly successful, improvements are still possible. For example, in some instances it may be desirable to concurrently diagnose the refractive errors of the eye using two or more different optical measurement devices so as to provide a better diagnosis (and treatment) of the refractive errors in the optical tissues of the eye. In order to take advantage of two different data sources for corneal treatment planning, however, the data from the two optical measurement devices must be registered.

Consequently, what is needed are methods, systems and software for registering datasets from separate optical measurement devices.

BRIEF SUMMARY OF THE INVENTION

The present invention provides methods, systems, and software for registering and aligning a first dataset of an object with a second dataset of the object. In one embodiment, the first and second datasets are a first optical measurement and a second optical measurement of an optical system.

In one aspect, the present invention provides a method of registering datasets obtained by two different instruments. The method comprises obtaining a first dataset from an object with a first instrument and obtaining a second dataset from the object with a second instrument. Distinctive data points of the object are located in each of the datasets and the distinctive data points are used to register the first dataset with the second dataset.

In one embodiment, the object is an eye that has refractive or other optical errors. The first optical measurement may be a wavefront measurement that is obtained by a wavefront measurement device. The second optical measurement may be a corneal topographical map obtained by a corneal topographer. Typically, the distinctive data points are one or more landmarks in the eye, such as a limbus, iris, iris center, iris pattern, pupil, pupil center, pupil boundary, and a corneal vertex.

In one embodiment, one of the landmarks is an iris center. Once the iris centers are located in both datasets, the iris centers are matched. If needed, a cyclotorsional offset between the other selected landmarks in the first dataset and the second dataset may be calculated and the cyclotorsional offset between the two datasets may be compensated for prior to overlaying the datasets with each other. A coordinate system transformation may be established between the two datasets to allow for the registration between the two optical measurements.

One or both of the datasets may also be scaled in size such that the first dataset and the second dataset substantially match each other, so that when the datasets are overlaid, the points on each of the datasets will be substantially registered and aligned with each other. Once the first and second datasets are registered and aligned, the datasets may be analyzed to diagnose the optical errors in the optical system. Thereafter, an ablation pattern for the optical system, based on the analysis of the registered first and second dataset, may be generated.

In another aspect, the present invention provides a method of improving a measurement of refractive errors of an optical system. The method comprises obtaining a first optical measurement of the optical system and obtaining a second measurement of the optical system. The first optical measurement of the eye is registered with the second measurement of the optical system.

The optical system typically comprises optical tissues of an eye, and the first measurement of the optical system may be a wavefront measurement of the eye and the second measurement may be a corneal topographical map of the eye. In one embodiment, registering the corneal topographical map of the eye with the wavefront measurement of the eye comprises locating landmarks in the corneal topographical map of the eye and the wavefront measurement of the eye and calculating at least one of a relative positional and torsional offsets between the landmarks to generate a coordinate system transformation between the topographical map and wavefront measurement. The landmarks include, but are not limited to, at least one of a limbus, iris, iris center, iris pattern, pupil, pupil center, pupil boundary, and a corneal vortex. The coordinate system transformation may be used to align the corneal topographical map of the eye with the wavefront measurement of the eye. The size of the corneal topographical map and the wavefront measurement may be scaled and/or overlayed with each other, if desired.

After the corneal topographical map and wavefront measurement are registered the optical errors of the eye may be diagnosed using the registered corneal topographical map and the wavefront measurement of the eye. Thereafter, an ablation pattern for the eye may be generated by analyzing at least one of the corneal ablation map and the wavefront measurement.

In a further aspect, the present invention provides a method of registering a corneal topographic map of an eye that is obtained by a first instrument with a wavefront measurement of an eye that is obtained by a second instrument. The method comprises locating landmarks in the corneal topographical map and locating a corresponding landmark in the wavefront measurement. The landmarks may be at least one of a limbus, iris, iris center, iris pattern, pupil, pupil center, pupil boundary, and a corneal vertex. A relative positional and torsional offset between the landmarks is determined and the corneal topographical map is registered with the wavefront measurement.

In another aspect, the present invention provides a system for registering a first dataset with a second dataset. The system comprises a memory coupled to a processor. The memory comprises a plurality of modules for registering the first dataset with the second dataset. The modules include a module for receiving the first dataset, a module for receiving the second dataset, a module for locating distinctive data points in each of the datasets; and a module for using the distinctive data points to register the first dataset with the second dataset.

The distinctive data points may be landmarks in an eye, such as a pupil center, pupil boundary, iris center, iris boundary, iris pattern, limbus, and/or a corneal vertex. The module for using the distinctive data points may be configured to calculate and compensate for a positional and torsional offset between the distinctive data points in the first dataset and second dataset.

The module for using the distinctive data points may be configured to overlay the first dataset with the second dataset The module for using the distinctive data points to register the first dataset with the second dataset may also be configured to scale a size of at least one of the first dataset and second dataset to substantially match the size of the datasets with each other.

The system may comprise a wavefront measurement device such that the first dataset is a wavefront measurement. The system may also include a corneal topographer such that the second dataset is a corneal topographical map. The modules of the system may also include a module for calculating an ablation pattern based on an analysis of the first dataset and the second dataset. The system may optionally include a laser assembly for delivering the ablation pattern.

In another aspect, the present invention provides a system for registering a first optical measurement of an optical system with a second optical measurement of the optical system. The system comprises a memory coupled to a processor. The memory comprises a plurality of modules for registering the first optical measurement with the second optical measurement. The modules comprise a module for obtaining the first optical measurement of the optical system, a module for obtaining the second optical measurement of the optical system, and a module for registering the first optical measurement of the optical system with the second optical measurement of the optical system.

The modules may further comprise a module for diagnosing the optical errors of the optical system. The diagnosing module may use the first optical measurement and the second optical measurement to diagnose the optical system. The modules may also include a module for generating an ablation pattern to correct the diagnosed optical errors of the optical system.

In one embodiment, the system of the present invention is configured to locate the same landmarks of the eye in two images from two separate devices, such as a VISX WaveScan® device and a Humphrey® ATLAS™ corneal topography system. Once the landmarks are located, the systems of the present invention may calculate relative positional and/or torsional offsets between the two sets of data (e.g., images) in order to align the datasets with each other.

In another aspect, the present invention provides a computer program stored on a computer-readable storage medium for measuring optical errors of an optical system. The computer program comprises a code module for receiving the first dataset, a code module for receiving the second dataset, a code module for locating distinctive data points in each of the datasets and a code module for using the distinctive data points to register the first dataset with the second dataset.

In one embodiment, the code modules are configured to receive wavefront measurements and or/ topographical map. The computer program may further include a code module for diagnosing optical errors of the optical system and a code module for generating an ablation pattern to correct the optical errors, wherein the ablation pattern is at least in part based on the diagnosis of the optical errors of the optical system.

In another aspect, the present invention provides a computer program stored on a computer-readable storage medium for registering a first optical measurement of an optical system with a second optical measurement of the optical system. The computer program comprises a code module for obtaining a first optical measurement of the optical system, a code module for obtaining a second optical measurement of the optical system, and a code module for registering the first optical measurement of the optical system with the second optical measurement of the optical system.

For a further understanding of the nature and advantages of the invention, reference should be made to the following description taken in conjunction with the accompanying drawings.

DETAILED DESCRIPTION OF THE INVENTION

The present invention is particularly useful for improving the diagnosis of optical errors of an eye and enhancing the accuracy and efficacy of laser eye surgical procedures to correct the optical errors of the eye, such as photorefractive keratectomy (PRK), phototherapeutic keratectomy (PTK), laser in situ keratomileusis (LASIK), laser epithelial keratomileusis (LASEK), and the like.

While the present invention is described primarily in the context of improving diagnosis and treatment of the refractive errors of the eye using a laser eye surgery system, it should be understood the present invention may be adapted for use in alternative diagnosis of other optical systems, eye treatment procedures, and optical systems such as femtosecond lasers and laser treatment, infrared lasers and laser treatments, radial keratotomy (RK), scleral bands, follow up diagnostic procedures, and the like.

Furthermore, while the remaining discussion focuses on registering and aligning datasets and images of an eye from a wavefront measurement system and a corneal topographer, the present invention is equally applicable to registering and aligning datasets obtained by a variety of other optical measurement instruments. For example, the present invention may be used to align images of any combination of a wavefront measurement system, a pupil camera on a wavefront measurement system, a corneal topographer, pachimetry devices, optical coherence tomography (OCT) scanners, any instrument that takes an image of the eye with the pupil and part of the iris in the field of view, and the like.

Figure 1:
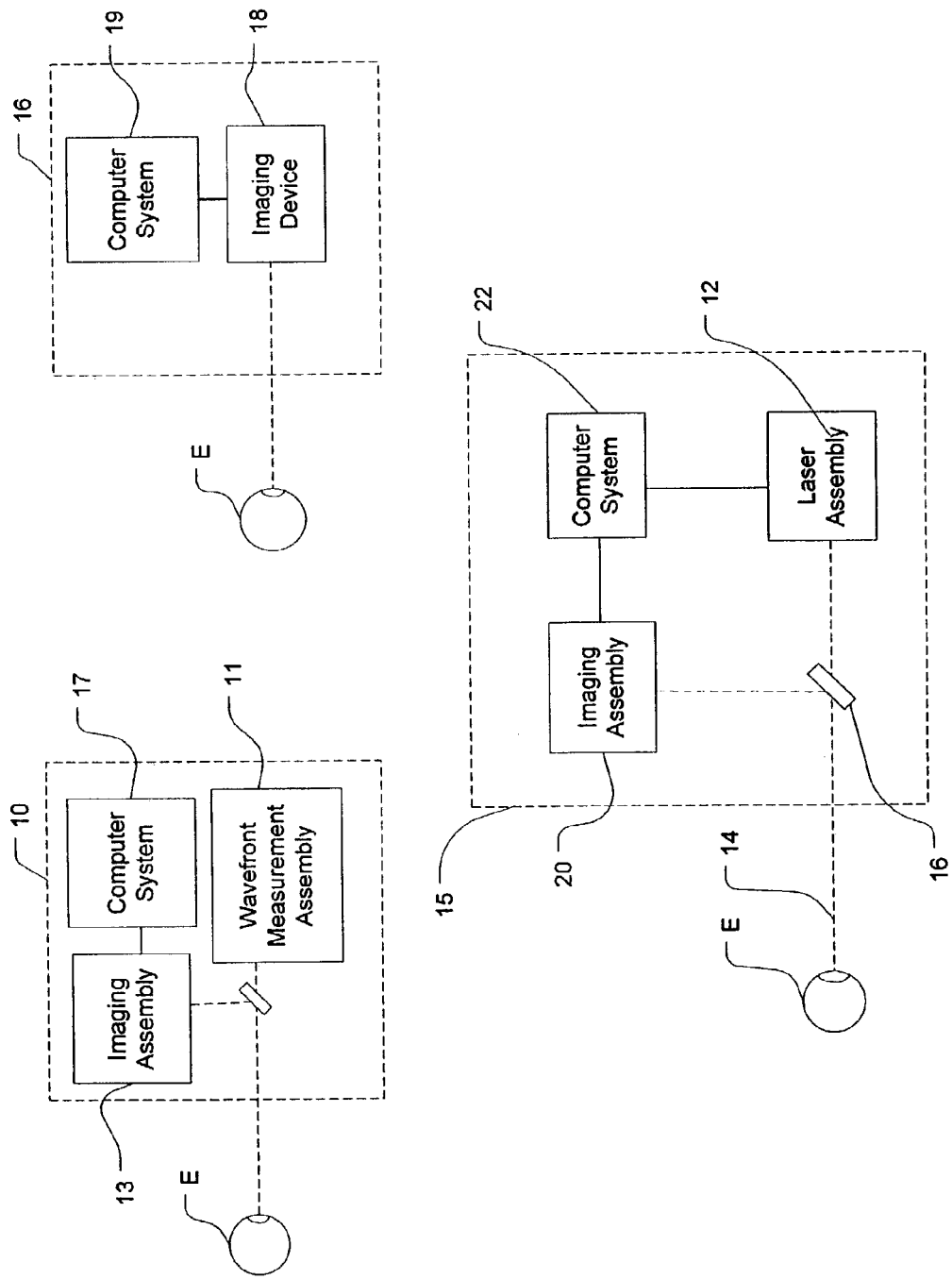
FIG. 1 schematically illustrates a simplified system according to an embodiment of the present invention.

FIG. 1 schematically illustrates a simplified system of one embodiment of the present invention. The illustrated system of the present invention typically includes a first measurement instrument 10, a second measurement instrument 16, and a laser system 15.

In one embodiment, the first measurement instrument is a wavefront measurement device 10 that measures aberrations and other optical characteristics of an entire ocular or other optical tissue system. The data from such a wavefront measurement device may be used to generate an optical surface from an array of optical gradients. It should be understood that the optical surface need not precisely match an actual tissue surface, as the gradients will show the effects of aberrations which are actually located throughout the ocular tissue system. Nonetheless, corrections imposed on an optical tissue surface so as to correct the aberrations derived from the gradients should correct the optical tissue system. As used herein terms such as "an optical tissue surface" may encompass a theoretical tissue surface (derived, for example, from wavefront sensor data), an actual tissue surface, and/or a tissue surface formed for purposes of treatment (for example, by incising corneal tissues so as to allow a flap of the corneal epithelium to be displaced and expose the underlying stroma during a LASIK procedure).

The second measurement instrument may be a corneal topographer 16. Corneal topographer 16 may be used to diagnose and examine the corneal surface. Corneal topographer 16 typically includes an imaging device 18, such as a frame grabber that takes images of the cornea. The images obtained by the frame grabber are analyzed by a computer system 19, and the computer system may generate one or more graphical and tabular outputs, including three dimensional topographical maps. Corneal topographer 16 may determine the contours of the corneal surface by measuring the elevations and depressions in the corneal surface. One example of a corneal topographer is the Humphrey® AtlaS™ Corneal Topographer, from Zeiss Humphrey Systems, of Dublin, Calif., which is an instrument that uses placido disk technology to generate images of the corneal surface.

Corneal topographer 16 may be based on a method that captures the reflection of rings of light off of the surface of the cornea and measures the distortion in the reflected light. A detector (not shown) captures the reflected images and computer system 19 processes the data, and displays the information in one or more formats selected by the user. For example, corneal topographer 16 may provide an axial map (which describe the radius of the curvature of the cornea relative to optic axis), curvature maps (which portray the radius of the curvature independent of the optic axis), and/or elevation maps (which illustrate the radius relative to a reference sphere).

As can be appreciated, the Humphrey® Atlas™ topographer is merely one example of a corneal topographer that may be used with the present invention. Other corneal topographers sold by Topcon Medical Systems, Dicon Diagnostics, Haag-Streit, EyeQuip, Tomey Corp., Bausch & Lomb, Carl Zeiss Ophthalmic Systems, Nidek, and Laser Sight may be used with the present invention. Some systems and methods for measuring a corneal topography of an eye are described in U.S. Pat. Nos. 4,761,071, 4,995,716, 5,406,342, 6,396,069, 6,116,738, 4,540,254 and 5,491,524, the full disclosures of which are incorporated herein by reference.

Figure 2:
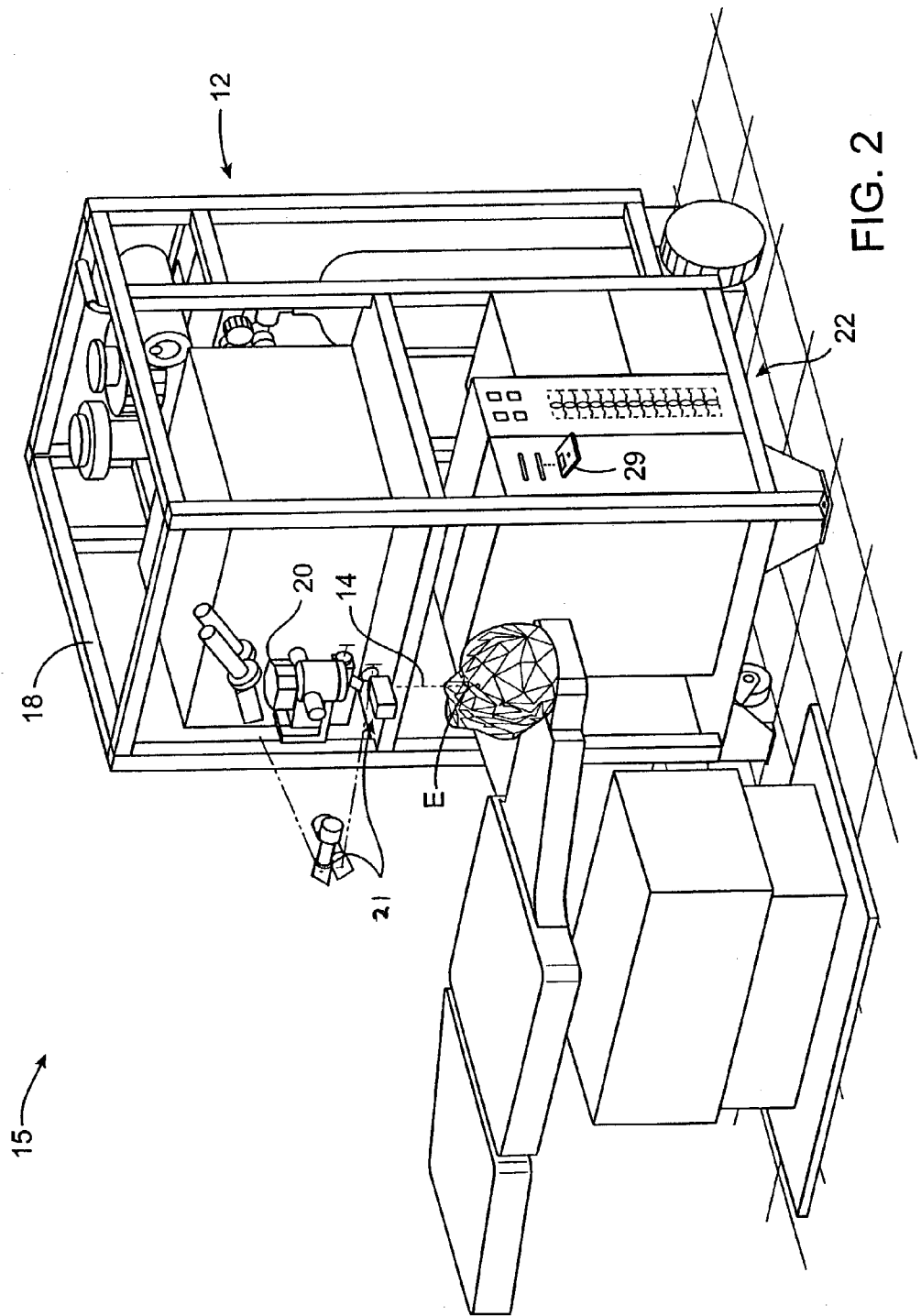
FIG. 2 schematically illustrates one exemplary laser system according to one embodiment of the present invention.

FIGS. 1 and 2 illustrate one embodiment of laser surgery system 15 that is encompassed by the present invention. Laser eye surgery system 15 includes a laser assembly 12 that produces a laser beam 14. Laser assembly 12 is optically coupled to laser delivery optics 21, which directs laser beam 14 to an eye of patient P. A delivery optics support structure (not shown here for clarity) extends from a frame 18 supporting laser assembly 12. An imaging assembly 20, such as a microscope is mounted on the delivery optics support structure to image a cornea of eye E during the laser procedure.

Laser assembly 12 generally comprises an excimer laser source, typically comprising an argon-fluorine laser producing pulses of laser light having a wavelength of approximately 193 nm. Laser assembly 12 will preferably be designed to provide a feedback stabilized fluence at the patient's eye, delivered via delivery optics 21. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 215 nm and/or those which utilize frequency-multiplying techniques. Hence, although an excimer laser is the illustrative source of an ablating beam, other lasers may be used in the present invention.

Laser assembly 12 and delivery optics 21 will generally direct laser beam 14 to the eye of patient P under the direction of a computer system 22. Computer system 22 will generally selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 21 will be under computer control of computer system 22 to effect the desired laser sculpting process so as to deliver the customized ablation profile, with the computer system ideally altering the ablation procedure in response to inputs from the optical feedback system. The feedback will preferably be input into computer system 22 from an automated image analysis system, or may be manually input into the processor by a system operator using an input device in response to a visual inspection of analysis images provided by the optical feedback system. Computer system 22 will often continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in commonly owned U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over the surface of the eye and controlling the number of pulses and/or dwell time at each location, as described, for example, by U.S. Pat. Nos. 4,665,913 (the full disclosure of which is incorporated herein by reference) and as demonstrated by other scanning laser systems such as the LSX laser by LaserSight, LadarVision by Alcon/Autonomous, Allegretto by Wavelight, and the 217C by Technolas; using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 15, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

As shown schematically in FIG. 1, wavefront measurement device 10 typically includes a wavefront measurement assembly 11 and an imaging assembly 13. Wavefront measurement assembly 11 can be used to measure and obtain a wavefront elevation surface of at least one of the patient's eyes and imaging assembly 13 and may simultaneously obtain still or moving images of the patient's eye during the wavefront measurement.

In exemplary embodiments, imaging assembly 13 is a CCD camera that can obtain a still image of the patient's eye. The image(s) obtained by imaging assembly 13 can thereafter be used to register the wavefront measurement and/or a customized ablation pattern (based on the wavefront measurement and/or corneal topography map) with the patient's eye during the laser surgical procedure.

The wavefront measurement assembly 11 and imaging assembly 13 can be coupled to or integral with a computer system 17 that can generate and store the wavefront measurements and images of the patient's eye. Thereafter, the patient's wavefront data can be stored on a computer readable medium 29, such as a CD-R, CD-RW, DVD-R, floppy disk, optical disk, a hard drive, or other computer readable medium. Optionally, in some embodiments, the computer system of the wavefront measurement device may also generate and save an ablation profile based on the wavefront data on the computer readable medium 29.

The still image of the eye, wavefront data, and/or the customized ablation profile can be loaded into a memory of laser surgical system 15 through reading of computer readable medium 29 or through delivery into the memory of surgical system 15 over a local or wide-area network (LAN or WAN). Laser eye surgery system 15 can include a computer system 22 that is in communication with an imaging assembly 20 and a laser assembly 12. Computer system 22 can have software stored in a memory and hardware that can be used to control the delivery of the ablative energy to the patient's eye, the tracking of the position of the patient's eye relative to an optical axis of laser beam 14 (e.g., translations in the x, y, and z directions and torsional rotations), and the like. In exemplary embodiments, among other functions, computer system 22 may be programmed to calculate a customized ablation profile based on the wavefront data and/or the corneal topography data, register the image(s) taken with imaging assembly 13 with the real-time image(s) taken by imaging assembly 20. Additionally, computer system 22 can be programmed to measure, in real-time, the movement (x(t), y(t), z(t), and rotational orientation θ(t)) of the patient's eye relative to the optical axis of the laser beam so as to allow the computer system to modify the delivery of the customized ablation profile based on the real-time position and/or orientation of the patient's eye.

Figure 3:
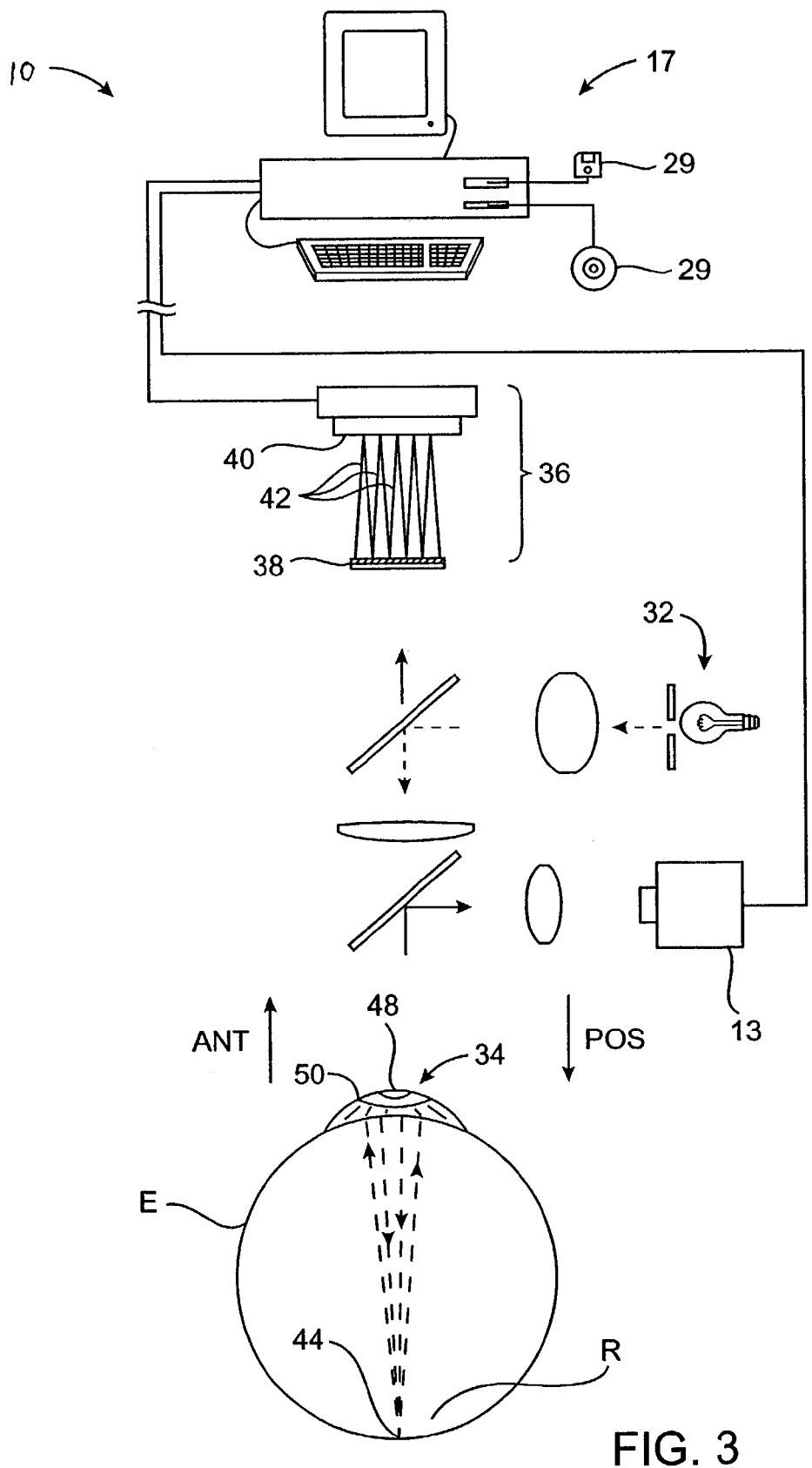
FIG. 3 illustrates a wavefront measurement device according to an embodiment of the present invention.

Referring now to FIG. 3, one embodiment of a wavefront measurement device 10 of the present invention is schematically illustrated. As can be appreciated, the illustrated wavefront measurement device 10 is merely an example of one wavefront measurement device that can be used with the embodiments of the present invention and other conventional or proprietary wavefront measurement devices can be used.

In very general terms, wavefront measurement device 10 includes an imaging assembly 13 that can image the patient's eye E during the wavefront measurement of the eye with the wavefront measurement assembly 11. Wavefront measurement assembly 11 includes an image source 32, such as a laser, which projects a source image through optical tissues 34 of eye E and so as to form an image 44 upon a surface of retina R. The image from retina R is transmitted by the optical system of the eye (specifically, optical tissues 34) and imaged onto a wavefront sensor 36 by system optics 38. The imaging assembly 13 can be in communication with a computer system 17 to deliver the image(s) of the patient's eye to a memory in the computer system 17. If desired, wavefront sensor 36 may also be configured to communicate signals to computer 17 for determination of a corneal ablation treatment program. Computer 17 may be the same computer which is used to direct operation of the laser surgery system 15, or at least some or all of the computer components of the wavefront measurement device 10 and laser surgery system may be separate. Data from wavefront sensor 36 may be transmitted to laser system computer 22 via tangible media 29, via an I/O port, via an networking connection such as an intranet, the Internet, or the like.

Wavefront sensor 36 generally comprises a lenslet array 38 and an image sensor 40. As the image from retina R is transmitted through optical tissues 34 and imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or CCD, and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics may decrease lower order optical errors by compensating for spherical and/or cylindrical errors of optical tissues 34. Higher order optical errors of the optical tissues may also be compensated through the use of an adaptive optic element, such as a deformable mirror. Use of a laser image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have well-defined and accurately formed image 44 on retina R.

While the method of the present invention will generally be described with reference to sensing of an image 44 on the retina, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement assembly 11 by focusing on a fixation target, as described in U.S. Pat. No. 6,004,313, the full disclosure of which is incorporated herein by reference. By varying a focal position of the fixation target as described in that reference, optical characteristics of the eye may be determined while the eye accommodates or adapts to image a field of view at a varying distance. Further alternatives include rotating of the eye by providing alternative and/or moving fixation targets within wavefront measurement assembly 11.

The location of the optical axis of the eye may be verified by reference to the data provided from an imaging assembly 13, such as a pupil camera, that images the eye concurrently during the wavefront measurements. In the exemplary embodiment, imaging assembly 13 images pupil 50 and/or the iris so as to allow subsequent determination of a position and torsional orientation of the pupil and/or iris for registration of the wavefront sensor data relative to the optical tissues, as will also be described hereinbelow.

Figure 3A:
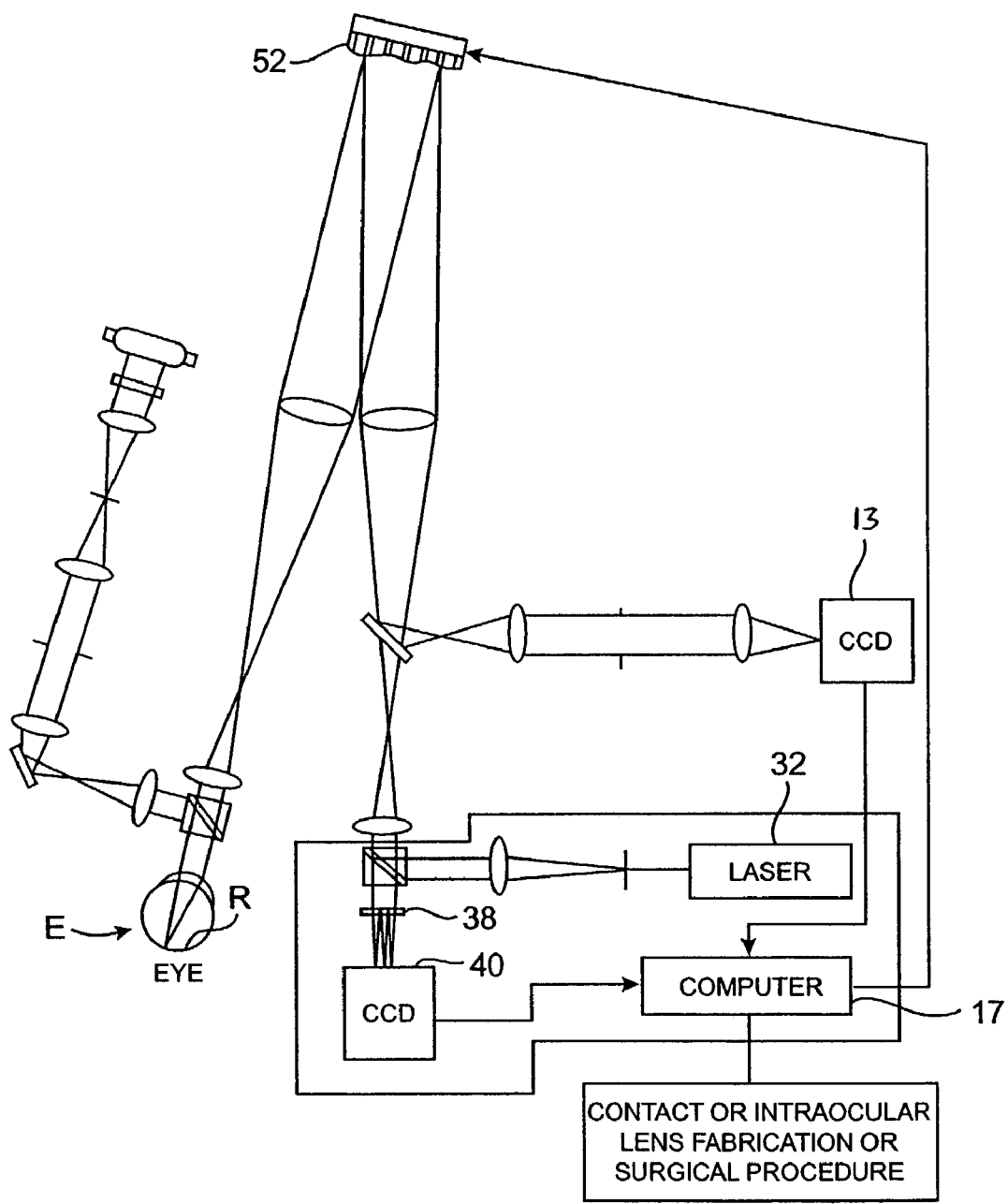
FIG. 3A illustrates an alternative wavefront measurement device of the present invention.

An alternative embodiment of a wavefront sensor system is illustrated in FIG. 3A. The major components of the system of FIG. 3A are similar to those of FIG. 3. Additionally, FIG. 3A includes an adaptive optical element 52 in the form of a deformable mirror. The source image is reflected from deformable mirror 52 during transmission to retina R, and the deformable mirror is also along the optical path used to form the transmitted image between retina R and imaging sensor 40. Deformable mirror 52 can be controllably deformed to limit distortion of the image formed on the retina, and may enhance the accuracy of the wavefront data. The structure and use of the system of FIG. 3A are more fully described in U.S. Pat. No. 6,095,651, the full disclosure of which his incorporated herein by reference.

The components of one embodiment of a wavefront system for measuring the eye and ablations comprise elements of a VISX WaveScan®, available from VISX, Incorporated of Santa Clara, Calif. A preferred embodiment includes a VISX WaveScan® with a deformable mirror as described above. An alternate embodiment of a wavefront measuring device is described in U.S. Pat. No. 6,271,915, the full disclosure of which is incorporated herein by reference.

Figure 4:
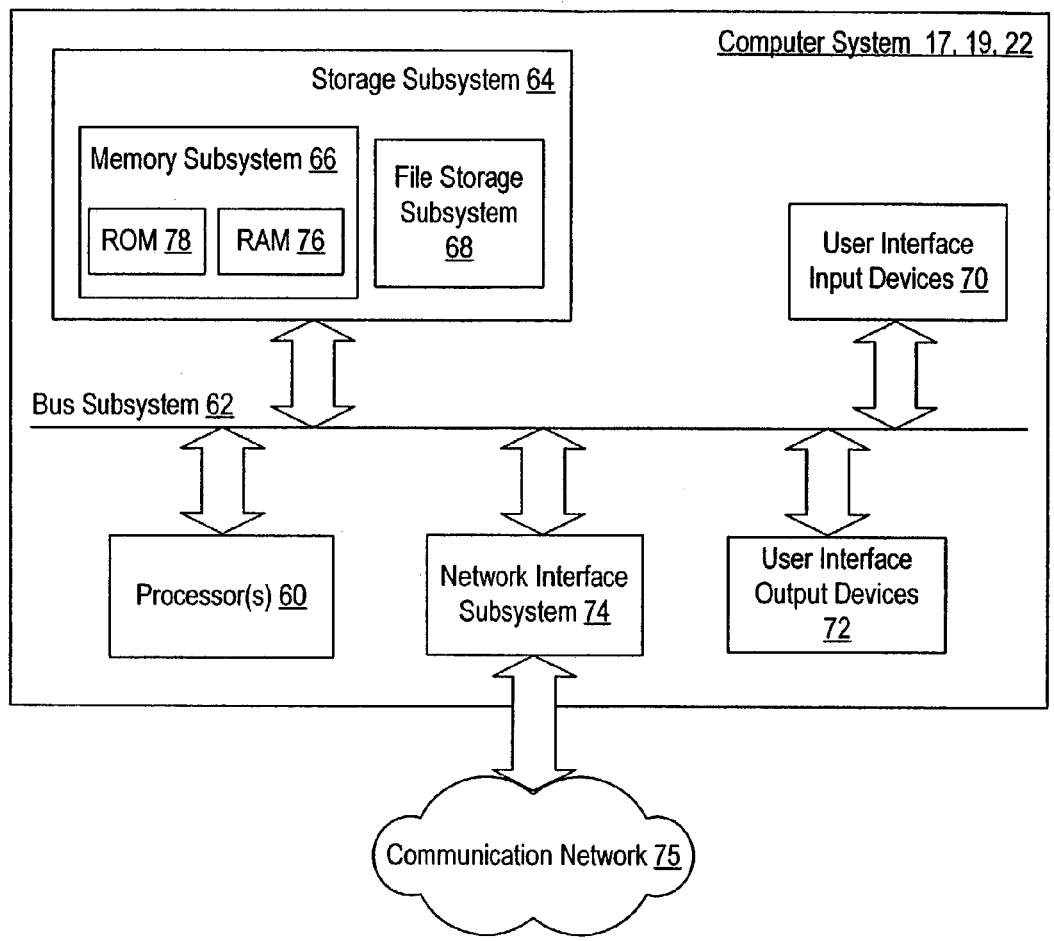
FIG. 4 schematically illustrates an exemplary computer system according to an embodiment of the present invention.

FIG. 4 is a simplified block diagram of an exemplary computer system 17, 19, 22 encompassed by the system of the present invention. The computer system typically includes at least one processor 60 which communicates with a number of peripheral devices via a bus subsystem 62. These peripheral devices may include a storage subsystem 64, comprising a memory subsystem 66 and a file storage subsystem 68, user interface input devices 70, user interface output devices 72, and a network interface subsystem 74. Network interface subsystem 74 provides an interface to a communication network 75 for communication with other imaging devices, databases, or the like.

User interface input devices 70 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. In general, use of the term "input device" is intended to include a variety of conventional and proprietary devices and ways to input information into the computer system. Such input devices will often be used to download a computer executable code from a computer network or a tangible storage media embodying steps or programming instructions for any of the methods of the present invention.

User interface output devices 72 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 64 stores the basic programming and data constructs that provide the functionality of the various embodiments of the present invention. For example, database and modules implementing the functionality of the present invention may be stored in storage subsystem 64. These software modules are generally executed by processor 60. In a distributed environment, the software modules may be stored in a memory of a plurality of computer systems and executed by processors of the plurality of computer systems. Storage subsystem 64 typically comprises memory subsystem 66 and file storage subsystem 68.

Memory subsystem 66 typically includes a number of memories including a main random access memory (RAM) 76 for storage of instructions and data during program execution and a read only memory (ROM) 78 in which fixed instructions are stored. File storage subsystem 68 provides persistent (non-volatile) storage for program and data files, and may include a hard disk drive, a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 68.

Bus subsystem 62 provides a mechanism for letting the various components and subsystems of the computer system communicate with each other as intended. The various subsystems and components of the computer system need not be at the same physical location but may be distributed at various locations within a distributed network. Although bus subsystem 62 is shown schematically as a single bus, alternate embodiments of the bus subsystem may utilize multiple busses.

The computer system itself can be of varying types including a personal computer, a portable computer, a workstation, a computer terminal, a network computer, a module in the imaging unit, a mainframe, or any other data processing system. Due to the ever-changing nature of computers and networks, the description of the computer system depicted in FIG. 4 is intended only as a specific example for purposes of illustrating one embodiment of the present invention. Many other configurations of the computer system are possible having more or less components than the computer system depicted in FIG. 4.

Figure 5:
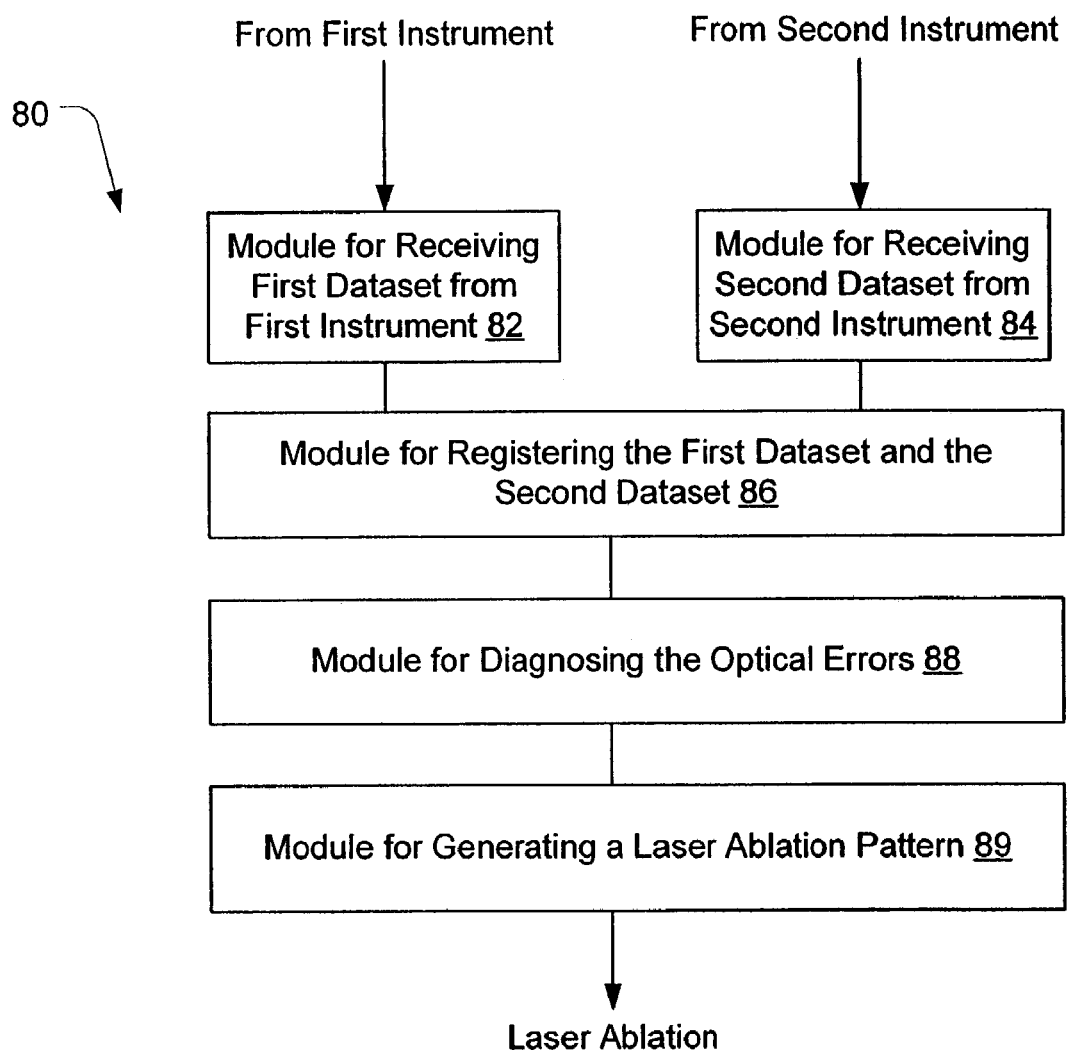
FIG. 5 schematically illustrates a method of the present invention as carried out by a plurality of modules.

FIG. 5 schematically illustrates a plurality of modules 80 that may carry out an embodiment of the present invention. The modules 80 may be software modules, hardware modules, or a combination thereof. If the modules are software modules, the modules will be embodied on a computer readable medium and processed by a processor 60 in any of computer systems of the present invention.

A first dataset from a first instrument will be received by module 82. The first dataset is typically an optical measurement and/or image of an optical system, such as an eye. For example, in one embodiment, the optical measurement is in the form of a wavefront measurement of a patient's eye. Such a wavefront measurement may be obtained by the wavefront measurement devices illustrated in FIGS. 3 and 3A. The second dataset from a second instrument will be received by module 84. The second dataset is also typically an optical measurement and/or image of the same optical system. For example, in one embodiment, the second optical measurement is in the form of a corneal topographical map of the patient's eye.

As can be appreciated, the present invention is not limited to a wavefront measurement device and a corneal topographer. The first instrument and second instrument can be any combination of optical measurement devices that are used for obtaining measurements of the optical or refractive errors of the optical system. The first and second dataset may be transmitted from the first instrument and second instrument over a communication network, or the datasets from each of the devices may be stored on a computer readable medium and uploaded to the computer system that is processing modules 80.

In order to take advantage of the two data sources (e.g., corneal topographer and wavefront measurement device) for diagnosis of refractive errors of the eye and for corneal treatment planning, the data from the two sources should be registered. Consequently, the first dataset and second data set are transmitted to module 86 where one or more image processing algorithms are applied to the datasets to register the first dataset and the second dataset. Typically, registration of the two datasets establishes a coordinate system transformation between the two datasets, to compensate for any positional and/or torsional misalignment.

Figure 6:
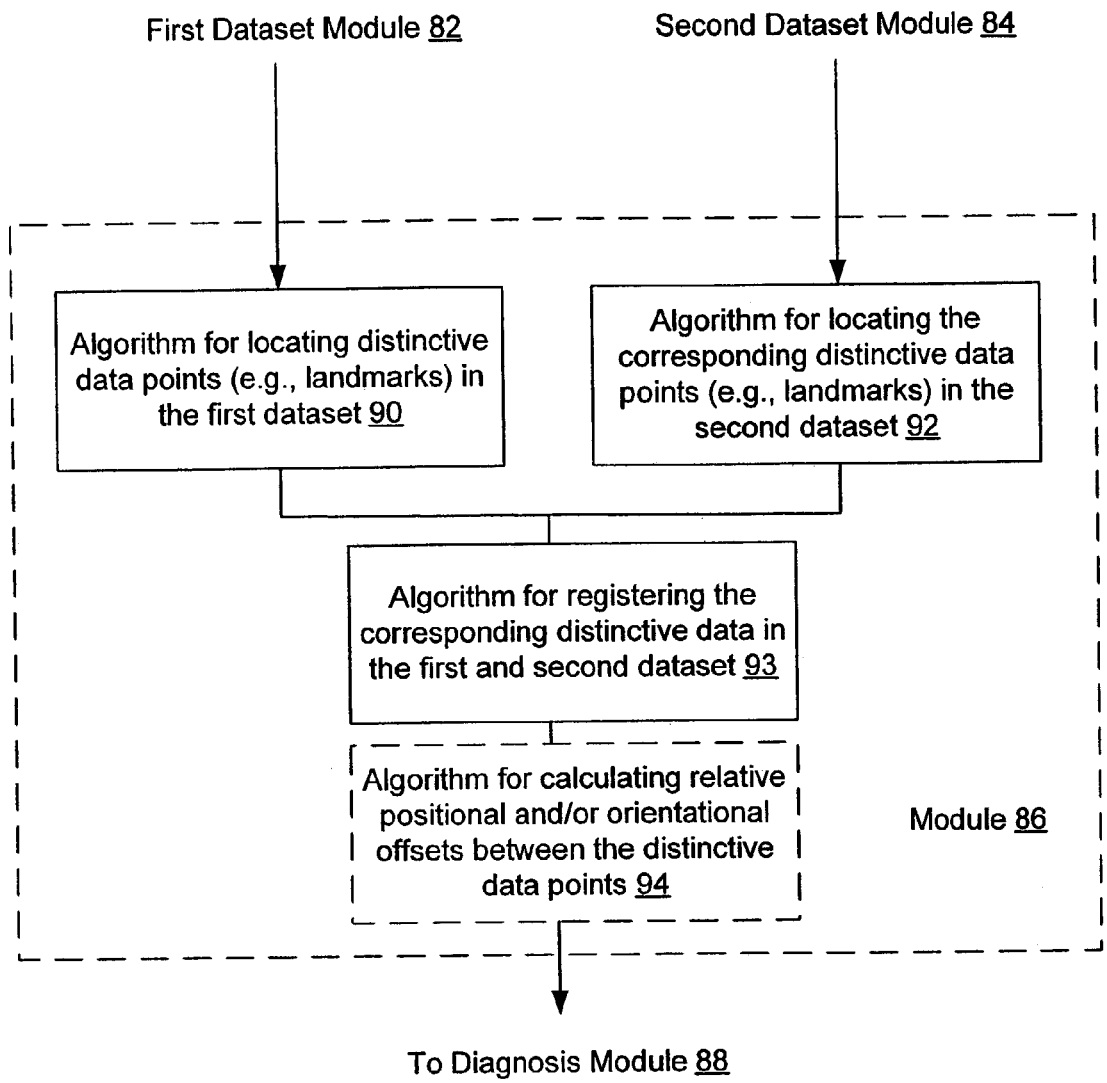
FIG. 6 illustrates one example of a module for registering the first dataset and the second dataset.

FIG. 6 schematically illustrates one exemplary embodiment of module 86. As can be appreciated however, FIG. 6 is merely one example of an image processing algorithm that may be used to register the two datasets, and the present invention should not be limited to the specific example of FIG. 6.

As illustrated, data from module 82 may be transmitted to module 86 where one or more algorithms are applied to the first dataset (e.g., wavefront measurement) to locate distinctive data points, such as landmarks in the wavefront measurement. Some examples of landmarks are the limbus, iris, iris boundary, iris center, iris pattern (e.g., texture of iris pattern), pupil, pupil center, cornea center, and corneal vertex. In one embodiment, illustrated in FIG. 6A, an algorithm 90 may detect the landmarks (e.g., pupil and the iris) with high accuracy.

In the illustrated embodiment, algorithm 90 calculates a pupil information (step 100), such as localizing a pupil, finding the center of the pupil, and/or calculating the radius of the pupil. In one embodiment the pupil is located by thresholding the dataset by analyzing a pixel value histogram and choosing the position of a first "dip" in the histogram after at least 2000 pixels are below the cutoff threshold. All pixels below the threshold may be labeled with "1" and pixels above the threshold are labeled with "0". Pixels labeled with "1" would generally correspond to the pupil, eyelashes, and possibly other regions of the image. It should be appreciated however, that the number of pixels employed will be related to the area of the pupil and will vary with applications of the invention.

The two distinguishing features about the pupil region, compared to other non-pupil regions is its large size and central location. In some embodiments, regions intersecting with a 5-pixel wide inner frame of the dataset may be discarded and the largest remaining region can be selected as the pupil.

If desired, the selected pupil region may be filled to remove any holes created by reflections, or the like. For example, in one embodiment, the remaining region of the image may also be analyzed for convexity. A radius and center of the pupil may be estimated by a standard weighted least-square estimation procedure.

Once the pupil information is calculated, the iris information may be calculated (step 102), such as locating an iris boundary, iris center, and iris radius. In some embodiments, the iris boundary may be estimated to be a certain radius of pixels (e.g., 320 pixels) and may be assumed to be constant for all people. The center of the iris may be calculated as a center of the circle that corresponds to the outer boundary of the iris. If desired, a position of the center of the iris may be used to calculate a pupil offset from the iris center.

Alternatively, another method of calculating the iris information takes advantage of the fact that the pupil center has already been found (as described above), that the iris has a limited range of possible values and the iris center is usually not very far from the pupil center. Since the center of the pupil and the center of the iris are typically not far from each other, it is possible to estimate the radial derivative of the image intensity with respect to the iris center by the radial derivative with respect to the pupil center. Furthermore, the limited range of iris radius values occurring in nature, allows restriction of a range of possible search to a ring centered at pupil center and having inner and outer radii such that the iris edge should always be located somewhere within the range. In one embodiment, the numerical search range, can be between approximately 10.5 mm and 14 mm. In other embodiments, the range may be larger or smaller, if desired.

Optionally, once the iris is found, the iris ring may then be unwrapped and divided into a fixed number of sectors, by converting the Cartesian iris coordinates into polar coordinates, centered at the pupil. (Step 104). In alternative embodiments, it may be possible to analyze the iris ring without unwrapping it. However, Applicant has found that unwrapping and scaling the iris ring allows better matching of landmarks (e.g., texture blocks) in the iris between different images of the eye by means of pure translation. For example, if the iris ring is not unwrapped, the algorithm may have trouble matching of texture blocks that have rotated, whereas if the iris ring is unwrapped, the texture blocks will maintain the same relative shape.

After the iris is divided into sectors, the landmarks may be located (step 106). For example, one salient region or landmark in each sector may be identified and its properties can be extracted. In one embodiment, the iris region is segmented into twenty four sectors of fifteen degrees. It should be appreciated, however, that in other embodiments, the iris region can be segmented into more than twenty four sectors or less than twenty four sectors.

The landmarks preferably are sufficiently distinct and have high contrast. There are several possible ways to select such landmarks. In one implementation, a square mask of size M×M (for example, 21×21 for dark-colored eyes and 31×31 for light-colored eyes) is defined. The mask can be scanned over each of the twenty four sectors, and for each pixel in each sector a value is computed from the region inside the mask centered at that pixel. The value assigned to the pixel is determined as the sum of amplitudes of all spatial frequencies present in the region. In one embodiment, the sum of the amplitudes can be computed by a Fourier transform of the region. If desired, the central 5×5 portion of the Fourier spectrum can be nulled to remove a DC component. The maximum value can then be located in each sector, such that the boundary of its corresponding mask is at least 5 pixels away from the iris boundary in order to avoid getting close to the pupil margin and other boundary artifacts, such as the eyelid and eyelashes. The "winning" positions and the corresponding blocks are stored for later comparison.

A more complete description of an algorithm that may be used to locate the center of the pupil, center of the iris, and other landmarks in a wavefront measurement image is described in U.S. patent application Ser. No. 10/300,714, filed on Nov. 19, 2002, and Groen, E., "Chapter 1 on Videooculography," PhD Thesis, University of Utrecht (1997), the complete disclosures of which are incorporated herein by reference.

Referring again to FIG. 6, the landmarks in the first dataset may be stored and the second dataset from module 84 may be transmitted to module 86 where algorithm 92 may used to locate the corresponding distinctive data points (e.g., pupil center, iris, landmarks, and the like) in the second dataset (e.g., corneal topography measurement). An algorithm similar to that shown in FIG. 6A may be used to locate the distinctive data points in the second dataset.

Unfortunately, in instances where the second dataset is from the corneal topographer, the image from the corneal topographer often contains reflections from the placido rings that are used by corneal topographer 16 to make the actual surface elevation computations. Presence of the placido rings often make it difficult to find the exact pupil center and boundary. However, algorithm 92 should be robust enough to accurately locate the pupil center and boundaries in the image.

Figure 6A:
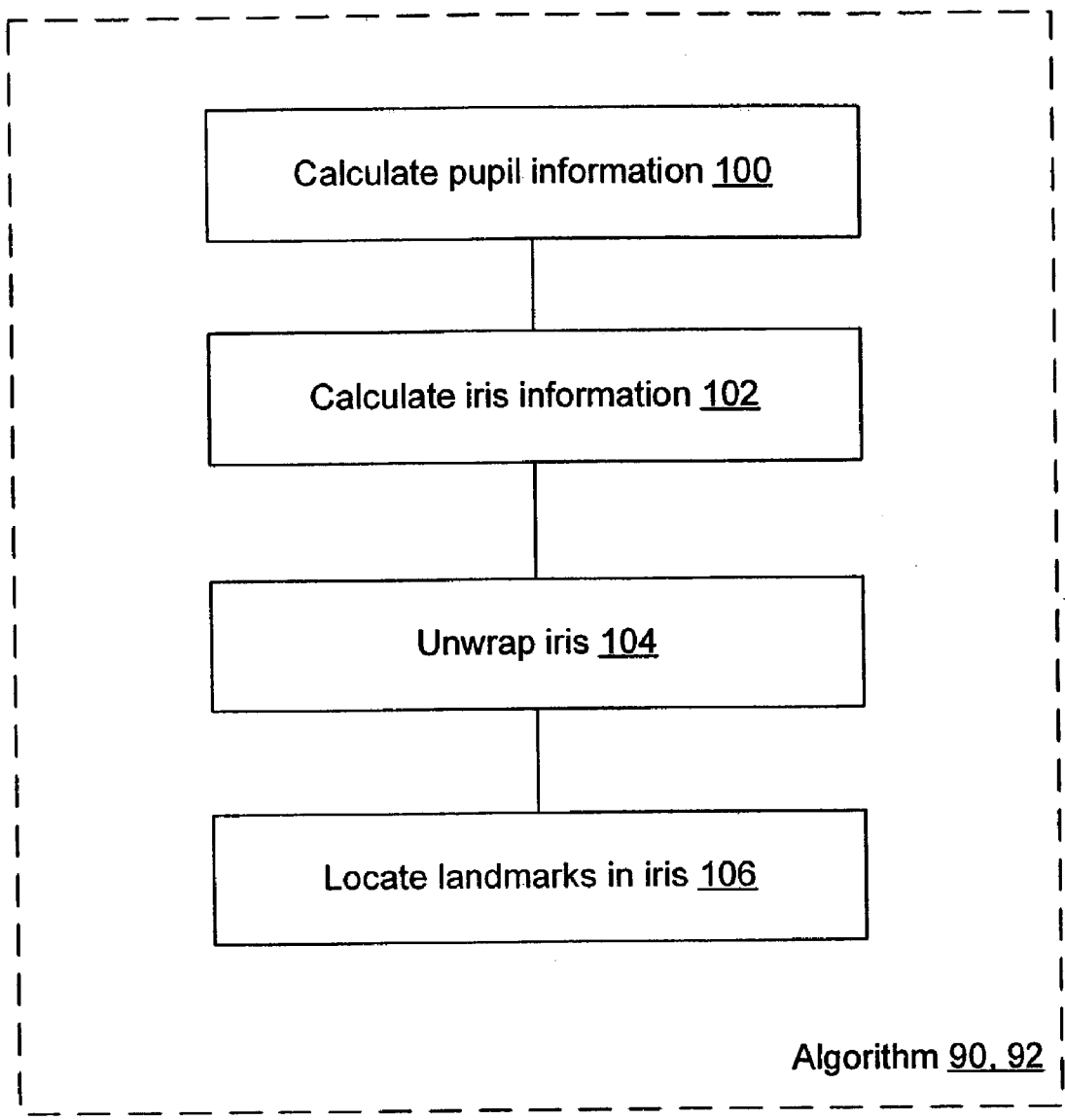
FIG. 6A illustrates one example of an algorithm for locating distinctive data points in a dataset.
Figure 6B:
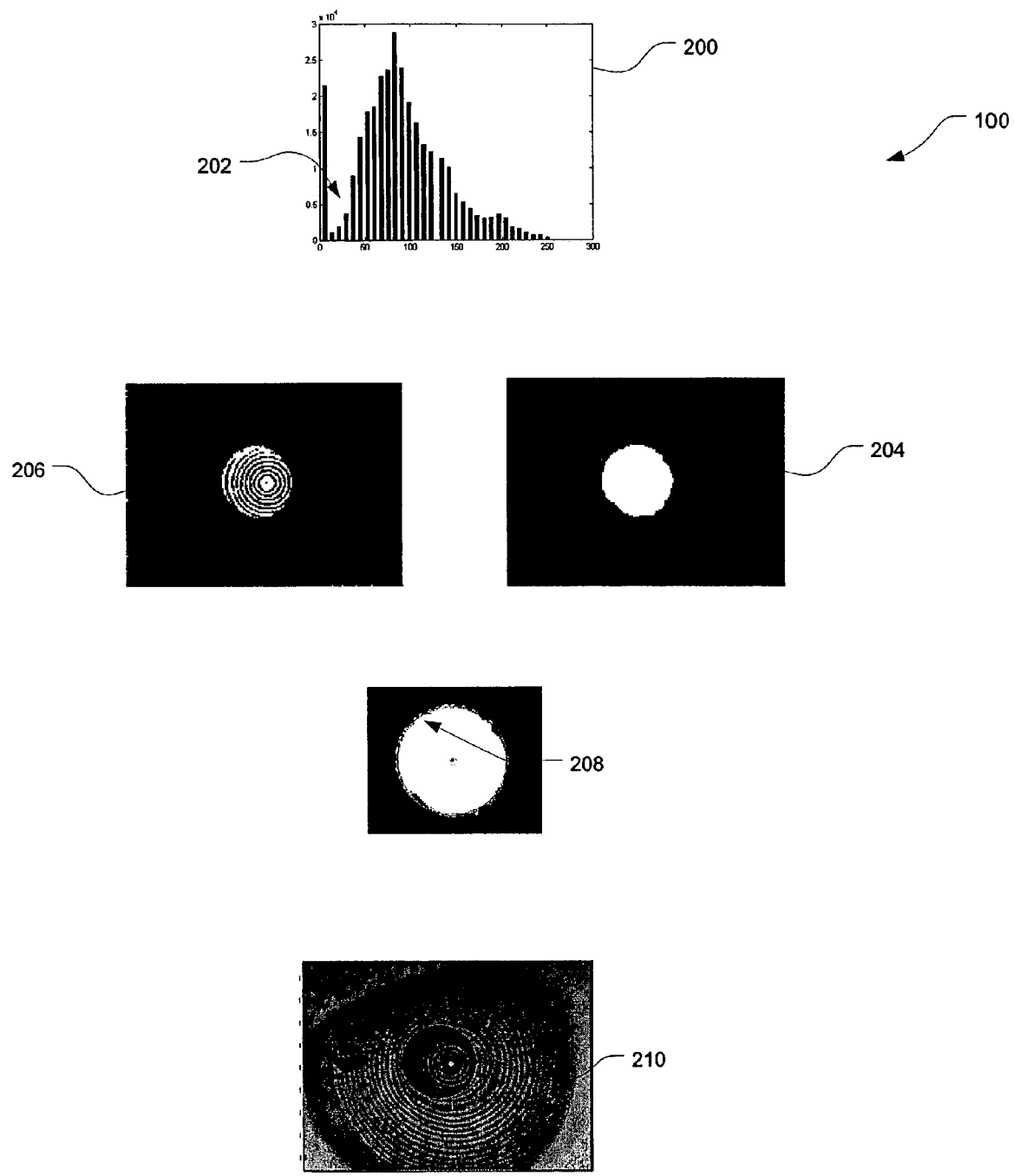
FIG. 6B illustrates one example of steps of locating a pupil center in a corneal topographical map.

FIG. 6B schematically illustrates one exemplary step 100 that may be used to locate the pupil in a corneal topography image. First, a threshold is determined based on an image histogram 200 to determine the boundary of the pupil. The first dip 202 is used to differentiate the pupil and the iris. The image may be thresholded 204 and is followed by a morphological dilation and erosion 206 to close the gaps from the rings. A best fitting circle is found, based on the region's boundary 208. The best fitting circle is deemed to be the outer boundary 210 of the pupil. From the outer boundary, the algorithm can locate the pupil center.

Additionally or alternatively, the outer edge of the iris remains partially visible and may be used to find the center of the cornea. Similar steps as illustrated in FIG. 6A may be used to locate the iris center, iris boundary, iris radius, and other landmarks in the iris, if desired. Some embodiments of such iris finding algorithms use the pupil center as an initial estimate of the center of the iris, but for the corneal topography map, it may be possible to use the center of the image as the initial estimate.

Figure 7:
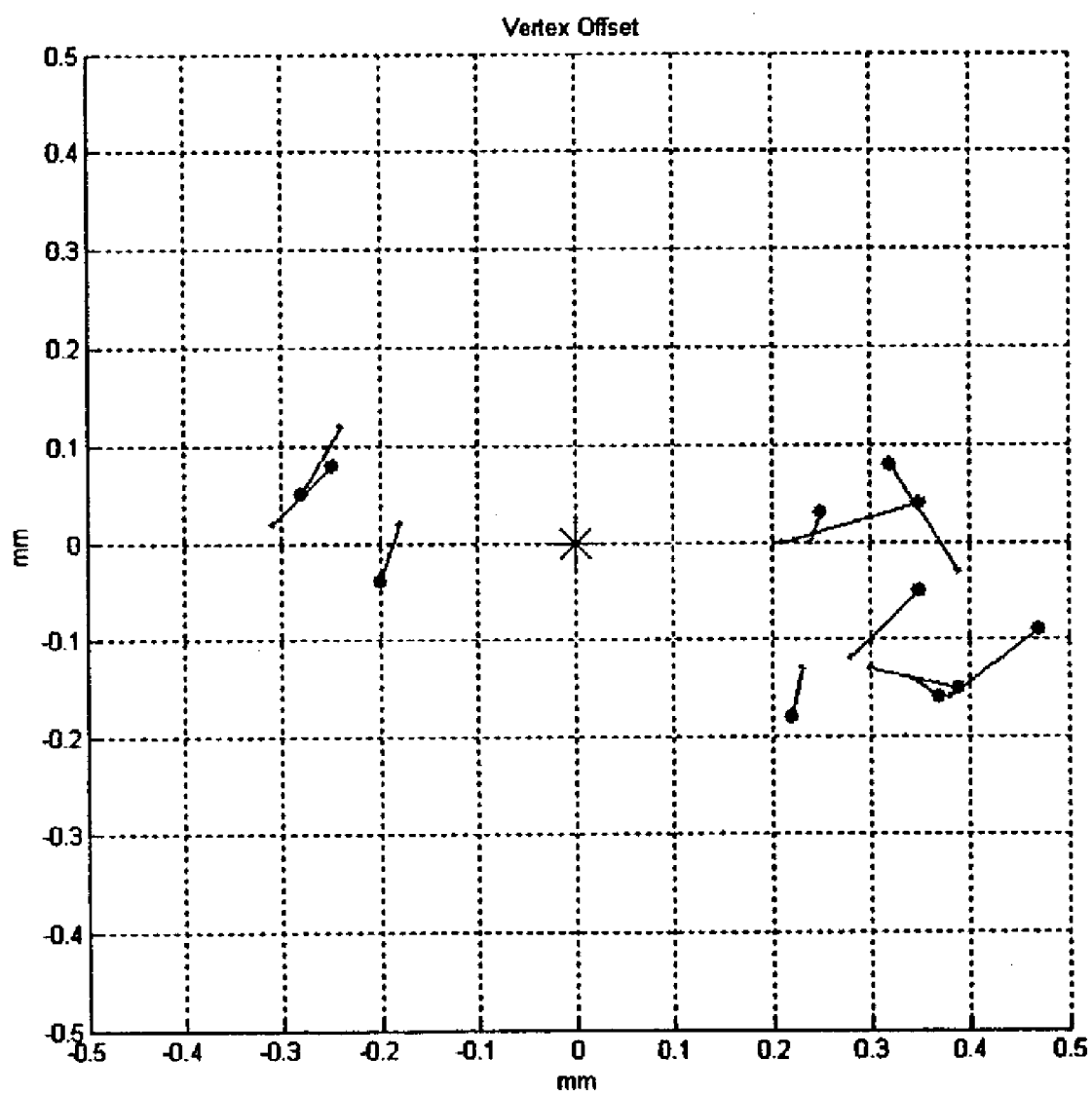
FIG. 7 is a graph which illustrates a relative change in estimated vertex position of measurement from a wavefront image and a corneal topography image.

FIG. 7 illustrates data from 11 eyes that were analyzed using the methods of the present invention. The iris size estimates were compared with the actual measured iris size. The mean difference in the estimated iris radius from the actual radius was 0.024 mm, with a standard deviation of 0.081 mm. The position of the corneal vertex with respect to the pupil center was compared for each of the pair of images. FIG. 7 shows a relative change in estimated vertex position for each pair. The darker dot represents the corneal vertex position from the wavefront data, while the lighter dot represents the corneal vertex position from the corneal topographer. The lines connecting the two dots indicate the estimated displacement.

Figure 8:
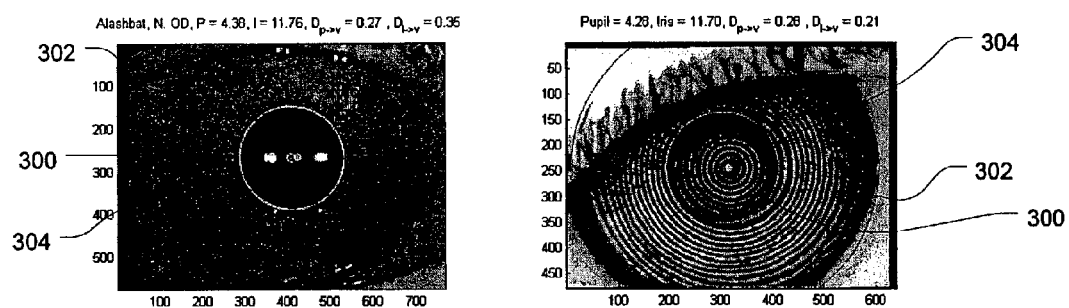
FIGS. 8 and 9 illustrate a plurality of images of a patient's eye and their calculated distinctive data points.
Figure 9:
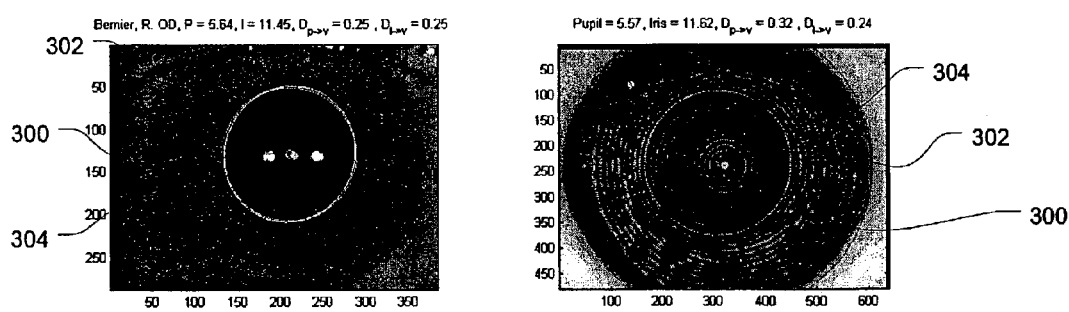

FIGS. 8 and 9 are some samples of applying the iris finding step to the corneal topography map dataset to locate the cornea center. Dot 300 indicates the calculated center of the iris as calculated by an algorithm of the present invention. Circle 302 with center 304 is the calculated center of the pupil in the images. Note the characteristic nasal displacement of the pupil center with respect to the corneal center on the topography images due to the smaller pupil size. FIG. 9 shows a similar set of data with the corneal topography map obtained by the corneal topographer 16. Because of the similar wavelengths, the iris pattern looks more similar between the two images. The wavefront measurement images the corneal vertex that corresponds to the first Purkinje reflection image from the measuring laser beam, while in the topography-based image, the vertex is the center of the innermost ring, which also contains Purkinje reflection images from the instrument target.

Referring again to FIG. 6, once the centers of the iris and/or other distinctive data points are located on both the first dataset and second dataset, module 93 is used to register the distinctive data points in the two datasets. The scale on one or both of the dataset images may be scaled and/or adjusted so that the first dataset and second dataset substantially match each other. If cyclorotation is discounted (e.g., due to the same body orientation and visual target orientation the cyclorotation is not significant), the two images may be overlaid, so that a region of the corneal topography that corresponds to the wavefront measurement can be selected and aligned, thus achieving registration.

As may be appreciated, even if the cyclorotation is not significant, if desired the landmarks may still be used to correct for the minor cyclorotation between the first and second dataset.

In some embodiments, an algorithm 94 may thereafter be used to calculate the relative positional and/or orientational offsets between the distinctive data points so as to determine the overall cyclotorsional difference between the two datasets, and the angle of rotation can be taken into account prior to the overlay of the two datasets, as described above and in patent application Ser. No. 10/300,714, filed Nov. 19, 2002, the complete disclosure of which was previously incorporated herein by reference.

Referring again to FIG. 5, once the first dataset and the second dataset are registered (module 86), the registered data may optionally be transmitted to module 88 where the datasets are analyzed, separately or in combination, to diagnose the optical errors in the optical system. Alternatively, the registered data may be manually analyzed by the physician to diagnose the optical errors. Once the optical errors of the optical system are diagnosed, one or both of the datasets are sent to module 89 where a laser ablation pattern is calculated.

In one embodiment, a treatment pattern such as an ablation program map may be calculated from the wavefront elevation map and/or corneal topography map so as to remove the regular (spherical and/or cylindrical) and irregular errors of the optical tissues. By combining the treatment program with a laser ablation pulse characteristics of a particular laser system, a table of ablation pulse locations, sizes, shapes, and/or numbers can be developed. Some exemplary methods and systems for preparing an ablation table are described in co-pending U.S. patent application Ser. No. 09/805,737 filed on Mar. 13, 2001 and entitled "Generating Scanning Spot Locations for Laser Eye Surgery," and Provisional Patent Application Ser. No. 60/389,090, filed Jun. 13, 2002 and entitled "Corneal Topography-Based Target Warping," the full disclosures of which is incorporated herein by reference. An ablation table may optionally be optimized by sorting of the individual pulses so as to avoid localized heating, minimize irregular ablations if the treatment program is interrupted, and the like.

As can be appreciated, in some embodiments, only one of the corneal topography map and the wavefront measurement may be used to generate the ablation pattern. For example, if only the corneal topography map is used, then all measurements are from the corneal surface, rather than the entire optical system of the eye. Some systems and methods for determining an ablation location and shape using corneal topography are described in U.S. Pat. Nos. 6,245,059, 6,129,722, and 5,843,070, the complete disclosures of which are incorporated herein by reference.

The corneal ablation pattern may be calculated by module 89 that is processed in a processor in computer system 17, 19, or 22, or by another separate processor for ablating the eye with laser ablation system 15 so as to correct the measured optical errors of the eye. The module 89 of the present invention may provide sophisticated modeling of the eye by taking into account the posterior surface of the cornea, model lens, etc. By using both the total aberrations (e.g., from the wavefront measurement) and the surface aberrations (e.g., from the corneal topographer) it may be possible to determine the sources of different aberrations in the eye and develop an ablation pattern that would minimize the size of the PSF (point spread function) on the retina, thus yielding optimal visual acuity for the patient. The two surfaces (e.g., wavefront and corneal topography) may be combined in various combinations (e.g., weighted average of wavefront and corneal topography) that would be determined from ray tracing through the various optical surfaces of the eye (both surfaces of the cornea and the lens) to create the retinal image. While purely wavefront-driven surgeries produced excellent outcome in patients, use of corneal topography might improve the consistency of results, screen for abnormal corneal surfaces and high amounts of lenticular aberrations, and determine the percentage of corneal aberrations relative to the internal aberrations in the optical system, thus leading to better diagnostic and outcomes of refractive treatments.

In one embodiment, module 89 is in a separate treatment planner system (not shown) that imports both the wavefront data and topography data. The calculations of the ablation profile will often be based on both the measured optical properties of the eye and on the characteristics of the corneal tissue targeted for ablation (such as the ablation rate, the refractive index, the propensity of the tissue to form "central islands" or decreased central ablation depths within a uniform energy beam, and the like). The results of the calculation will often comprise an ablation pattern in the form of an ablation table listing ablation locations, numbers of pulses, ablation sizes, and or ablation shapes to effect the desired refractive correction. An exemplary method for generating ablation patterns is described in co-pending U.S. patent application Ser. No. 09/805,737, the full disclosure of which was previously incorporated herein by reference. Where the refractive error is to be corrected by alternative treatment modalities, alternative treatment plans may be prepared, such as corneal ring implant sizes, or the like.

To torsionally align (i.e., register) the ablation profile with the patient's eye, the calculated ablation-profile needs tohave a unique coordinate transformation to an image of the eye taken by the pupil camera of the laser system so as to determine the positional differences and torsional offset between the ablation profile and the real-time image of the eye. In exemplary embodiments, the pupil camera is a video device that can obtain streaming video of the patient's eye. One frame of the streaming video, typically the first frame of the streaming video, can be analyzed by the computer system to locate the pupil center, iris center, and/or markers that were originally located in the first and/or second dataset. Once the pupil center, iris center, and/or markers are located, a torsional offset between the ablation pattern and video frame image of the patient's eye is calculated.

Once the torsional offset is determined, the computer system can track the translational position (x(t), y(t), and z(t)) of the patient's pupil with a high speed eye tracker (HSET) and the torsional orientation (θ(t)) of the eye with a torsional tracker. Because the position of the center of the pupil is typically tracked with the HSET, the torsional tracker generally estimates the position of the landmarks with respect to the pupil center. A more complete description of torsionally registering images of the eye and torsionally tracking the eye is described in commonly owned U.S. patent application Ser. No. 10/300,714, filed Nov. 19, 2002, the complete disclosure of which was previously incorporated herein by reference.

As will be understood by those of skill in the art, the present invention may be embodied in other specific forms without departing from the essential characteristics thereof. One of ordinary skill in the art would recognize other variations, modifications and alternatives. For example, while the present invention is described by registering two datasets, it should be appreciated, that the present invention may register three or more datasets, if desired. Moreover, the present invention may be used for diagnosis of aberration sources (e.g., corneal surface or internal aberrations), choosing optimal treatment with lens models, point spread function, and the like. Accordingly, the foregoing description is intended to be illustrative, but not limiting, of the scope of the invention which is set forth in the following claims.

What is claimed is:

1. A method of registering datasets of an eye obtained by two different instruments, the method comprising:
    obtaining a first high-order optical tissue surface shape dataset from an eye with a first instrument while the eye is aligned with the first instrument;
    obtaining a first image of the eye associated with the first dataset while the eye is aligned with the first instrument and while obtaining the first dataset;
    obtaining a second high-order optical tissue surface shape dataset from the eye with a second instrument while the eye is aligned with the second instrument while the eye is not aligned with the first instrument, the second instrument being separate from the first instrument;
    obtaining a second image of the eye associated with the second dataset while the eye is aligned with the second instrument and while obtaining the second dataset;
    locating a plurality of distinctive data points of the eye in each of the datasets, the distinctive data points for each dataset identified from the associated image by comparing calculating values from across the image; and
    using the distinctive data points to torsionally register the first dataset with the second dataset.

2. The method of claim 1 wherein the dataset from the first instrument comprises a time series of wavefront measurements of the eye.

3. The method of claim 2 wherein the distinctive data points comprise one or more landmarks in the eye.

4. The method of claim 3 wherein the landmarks comprise at least one of a limbus, iris, iris center, iris pattern, pupil, pupil center, pupil boundary, or corneal vertex.

5. The method of claim 3 wherein the distinctive data points comprise an iris center, wherein using the distinctive data points to register comprises matching the iris centers of the first data set and the second data set,
    the method further comprising scaling at least one of the dataset so that sizes of the first dataset and second data set substantially match each other.

6. The method of claim 2 further comprising generating an ablation pattern for the eye based on an analysis of the first dataset and second dataset.

7. The method of claim 1 further comprising overlaying the first data set and the second data set.

8. The method of claim 7 comprising measuring a cyclotorsional offset between the first dataset and second dataset and compensating for the cyclotorsional offset prior to overlaying the first data set and the second data set.

9. The method of claim 1 wherein using the distinctive data points comprises calculating relative positional and torsional offsets between the first data set and the second data set.

10. The method of claim 9 wherein calculating relative positional and torsional offsets comprises establishing a coordinate system transformation between the first data set and second data set.

11. The method of claim 1 wherein the first and second instruments comprise different types of instruments, and further comprising deriving a refractive treatment from the registered first and second datasets.

12. A method of registering datasets of an eye obtained by two different instruments, the method comprising:
    obtaining a first high-order corneal aberration dataset from an eye with a first instrument, wherein the dataset from the first instrument comprises a wavefront measurement of the eye;
    obtaining a second high order corneal surface shape dataset from the eye with a second instrument, wherein the second dataset from the second instrument comprises a corneal topographic map of the eye;
    locating distinctive data points of the eye in each of the datasets by identifying a plurality of sectors of an iris of the eye, the distinctive data points comprising iris pattern landmarks with one located iris pattern landmark being disposed in each of the sectors, and an iris or pupil center landmark;
    using the distinctive data points to register the first dataset with the second dataset by calculating relative positional offsets between the first data set and the second data set with the iris or pupil center landmarks, and by calculating relative torsional offsets between the first dataset and second dataset with the iris pattern landmarks; and
    scaling at least one of the datasets so that sizes of the first dataset and second dataset substantially match each other.

13. A method of improving a measurement of refractive errors of an optical system, the method comprising:
    obtaining a first high order optical measurement of a surface of the optical system with a first instrument;
    after the first optical measurement has been obtained, obtaining a second high order measurement of a surface of the optical system with a second instrument; and
    torsionally registering the first optical measurement of the optical system with the second measurement of the optical system in response to calculated imaging landmarks.

14. The method of claim 13 wherein the optical system comprises optical tissues of an eye, wherein the first or second measurement of the optical system comprises a time series of wavefront measurements of the eye and the other measurement comprises a corneal topographical map of the eye.

15. The method of claim 14 further comprising diagnosing the optical errors of the eye using the registered corneal topographical map and the wavefront measurement of the eye.

16. The method of claim 15 further comprising deriving a refractive treatment from the registered first and second measurements.

17. The method of claim 14 comprising generating an ablation pattern for the eye by analyzing at least one of the corneal ablation map and the wavefront measurement.

18. The method of claim 14 wherein registering the corneal topographical map of the eye with the wavefront measurement of the eye comprises:
locating landmarks in the corneal topographical map of the eye and the wavefront measurement of the eye;
calculating at least one of a relative positional and torsional offsets between the landmarks to generate a coordinate system transformation between the topographical map and wavefront measurement; and
using the coordinate system transformation to align the corneal topographical map of the eye with the wavefront measurement of the eye.

19. The method of claim 18 wherein the landmarks comprise at least one of a limbus, iris, iris center, iris pattern, pupil, pupil center, pupil boundary, or corneal vortex.

20. The method of claim 14 wherein registering comprises scaling a size of at least one of the corneal topographical map and the wavefront measurement.

21. The method of claim 14 wherein registering comprises overlaying the corneal topographical map of the eye with the wavefront measurement of the eye.

22. A system for registering a first high order optical surface dataset with a second high order optical surface dataset, each of the datasets including high order optical surface information with associated image information, the image information of the first dataset being different than the image information of the second dataset, the system comprising:
a processor;
a memory coupled to the processor, the memory comprising a plurality of modules of computer-implemented instructions embodied on a tangible computer medium for registering the first dataset with the second dataset, the modules comprising:
a module for receiving the first dataset of an eye, the high order optical surface information of the first dataset comprising a time series of wavefront data;
a module for receiving the second dataset of the eye;
a module for calculating distinctive imaging data points from the image information in each of the datasets of the eye; and
a module for using the distinctive data points to torsionally register the first dataset with the second dataset.

23. The system of claim 22 wherein the second dataset comprises a corneal topographical map.

24. The system of claim 22 Wherein the system further comprises a corneal topographer that obtains the second dataset.

25. The system of claim 22 wherein the system further comprises a wavefront measurement device that obtains the first dataset.

26. The system of claim 22 wherein the modules further comprise a module for calculating an ablation pattern based on the first dataset and the second dataset.

27. The system of claim 26 further comprising a laser assembly for delivering the ablation pattern.

28. The system of claim 22 wherein the module for using the distinctive data points to register the first dataset with the second dataset is configured to scale a size of at least one of the first dataset and second dataset to substantially match the datasets with each other.

29. The system of claim 22 wherein the distinctive data points comprise landmarks in the eye.

30. The system of claim 29 wherein the module for locating distinctive data points is configured to locate at least one of a pupil, pupil center, pupil boundary, iris center, iris pattern, iris boundary, limbus, and corneal vertex in the first and second datasets.

31. The system of claim 30 wherein the module for using the distinctive data points is configured to calculate and compensate for a positional and torsional offset between the distinctive data points in the first dataset and second dataset.

32. The system of claim 31 wherein the module for using the distinctive data points is configured to overlay the first dataset with the second dataset.

33. A system for registering a first high-order optical surface measurement of an optical system with a second high-order optical surface measurement of the optical system, the system comprising:
a processor;
a memory coupled to the processor, the memory comprising a plurality of modules with processor-implementable instructions embodied on a tangible medium for registering the first optical measurement with the second optical measurement, the modules comprising:
a module for obtaining the first optical measurement of the optical system and first image information obtained simultaneously with the first optical measurement of the optical system;
a module for obtaining the second optical measurement of the optical system and second image information obtained simultaneously with the second optical measurement of the optical system, the second image information obtained at a different time than the first image information; and
a module for torsionally registering the first optical measurement of the optical system with the second optical measurement of the optical system in response to imaging landmarks from the first and second image information.

34. The system of claim 33 further comprising a module for diagnosing the optical errors of the optical system using the first optical measurement and the second optical measurement of the optical system.

35. The system of claim 34 further comprising a module for generating an ablation pattern to correct the diagnosed optical errors of the optical system.

36. A system for measuring optical errors of an optical system of an eye, the system comprising:
means for obtaining a first high-order optical surface measurement of the optical system while the eye is at a first location;
means for obtaining a second high-order optical surface measurement of the optical system while the eye is at a second location; and
means for torsionally registering, in response to calculated imaging landmarks, the first optical measurement of the optical system with the second optical measurement of the optical system.

37. The system of claim 36 further comprising means for diagnosing the optical errors of the optical system using the first optical measurement and the second optical measurement of the optical system.

38. The system of claim 37 further comprising means for correcting the diagnosed optical errors of the optical system.

39. A computer program of code modules stored on a computer-readable storage medium for measuring optical errors of an optical system, the computer program comprising:
- a code module for receiving a first high-order optical surface dataset of the optical system;
- a code module for receiving a second high-order optical surface dataset of the optical system;
- a code module for locating distinctive calculated data points in each of the datasets of the optical system; and
- a code module for using the distinctive data points to torsionally register the first dataset with the second dataset when a location of the optical systems is different for the second dataset and the first dataset.

40. The computer program of claim 39 wherein the first dataset comprises a wavefront measurement.

41. The computer program of claim 39 or 40 wherein the second dataset is a topographical map.

42. The computer program of claim 39 further comprising a code module for diagnosing the optical errors of the optical system.

43. The computer program of claim 42 comprising a code module for generating an ablation pattern to correct the optical errors, wherein the ablation pattern is at least in part based on the diagnosis of the optical errors of the optical system.

44. A computer program of code modules stored on a computer-readable storage medium for registering a first high-order optical measurement of an optical system of an eye with a second high-order optical measurement of the optical system, the computer program comprising:
- a code module for obtaining the first optical surface measurement of the optical system;
- a code module for obtaining the second optical surface measurement of the optical system; and
- a code module for identifying, from calculated imaging values, distinctive data points in each optical surface measurement; and
- a code module for torsionally registering the first optical measurement of the optical system with the second optical measurement of the optical system in response to the distinctive data points when a location of the eye is different fro the second measurement and the fist measurement.

45. The computer program of claim 44 further comprising a code module for diagnosing the optical errors of the optical system using the first optical measurement and the second optical measurement of the optical system.

46. The computer program of claim 45 further comprising a code module for generating an ablation pattern to correct the diagnosed optical errors of the optical system.

47. A method of registering a corneal topographic map of an eye that is obtained by a first instrument with a wavefront measurement of the eye that is obtained by a second instrument, the method comprising:
- locating, from calculated image values, a plurality of imaging landmarks in a first image of the eye associated with the corneal topographical map;
- locating a plurality of corresponding imaging landmark in a second image of the eye associated with the wavefront measurement, the second image of the eye being different than the first image of the eye;
- determining a relative positional and torsional offset between the landmarks; and
- registering the corneal topographical map with the wavefront measurement.

48. The method of claim 47 wherein the landmarks comprise at least one of a limbus, iris, iris center, iris pattern, pupil, pupil center, pupil boundary, and corneal vertex.

49. The method of claim 47 further comprising overlaying the corneal topographical map with the wavefront measurement.

* * * * *